United States Patent [19]

Mueller

[11] 3,992,375

[45] Nov. 16, 1976

[54] DIBENZOXAZEPINE N-CARBOXYLIC ACID HYDRAZINES AND DERIVATIVES

[75] Inventor: Richard A. Mueller, Glencoe, Ill.

[73] Assignee: G. D. Searle & Co., Chicago, Ill.

[22] Filed: Aug. 25, 1975

[21] Appl. No.: 607,214

Related U.S. Application Data

[60] Division of Ser. No. 496,692, Aug. 12, 1974, Pat. No. 3,917,649, which is a continuation-in-part of Ser. Nos. 127,360, March 23, 1971, abandoned, and Ser. No. 329,407, Feb. 5, 1973, abandoned.

[52] U.S. Cl. .................... 260/240 J; 260/240 R
[51] Int. Cl.$^2$ ........................ C07D 267/20
[58] Field of Search ............. 260/333, 240 J, 240 R

[56] References Cited
UNITED STATES PATENTS 3,534,019   10/1970   Coyne et al. ..................... 260/239
3,624,104   11/1971   Cusic ................................ 260/333

OTHER PUBLICATIONS

William E. Coyne et al., Jour. Med. Chem., 11 (6), (1968), pp. 1158–1160.

Primary Examiner—Norma S. Milestone
Attorney, Agent, or Firm—John J. McDonnell

[57] ABSTRACT

Derivatives of the dibenzoxazepine N-carboxylic acid hydrazides are acylated to yield N,N'-diacyl hydrazines which are useful pharmacological agents as is evidenced by their anti-arrhythmic, anti-inflammatory, anti-diarrheal, prostaglandin antagonist and 5-hydroxytryptamine antagonist activity.

2 Claims, No Drawings

DIBENZOXAZEPINE N-CARBOXYLIC ACID HYDRAZINES AND DERIVATIVES

This is a division, of application Ser. No. 496,692, filed Aug. 12, 1974, now U.S. Pat. No. 3,917,649, which in turn is a continuation-in-part of my copending application Ser. No. 127,360, filed Mar. 23, 1971, now abandoned, and Ser. No. 329,407, filed Feb. 5, 1973 and now abandoned.

This invention is concerned generally with derivatives of the dibenzoxazepine N-carboxylic acid hydrazides and more specifically with compounds of the following general formula

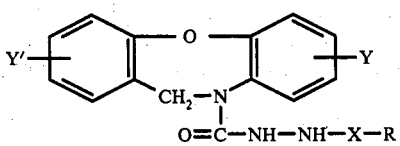

wherein Y and Y' are hydrogen, halogen, methyl or trifluoromethyl, X is carbonyl or sulfonyl and when X is carbonyl, R is hydrogen, perfluoroalkyl, carboxyalkenyl, alkenyl, aryloxyalkyl, carboxyalkyl, haloalkyl, haloaryloxyalkyl, aralkenyl or cyanoalkyl, and when X is sulfonyl, R is alkyl, haloalkyl, aryl or aralkyl. The alkyl radicals intended contain 1–12 carbon atoms and are illustrated by methyl, ethyl, propyl, butyl, and the corresponding branched-chain isomers. The halo radicals intended are chlorine, iodine, bromine and fluorine. The alkenyl radicals comprehended contain 1–12 carbon atoms and are typified by vinyl, propenyl, butenyl, pentenyl, hexenyl, heptenyl, octenyl, nonenyl, decenyl, undecenyl, dodecenyl and the branched-chain isomers thereof. Typical of the aryl radicals denoted in the foregoing formula are phenyl, tolyl and xylyl, while the aralkyl radicals are illustrated by benzyl, phenethyl, etc., and the aralkenyl radicals by phenalkenyl groups such as cinnamyl, phenallyl, etc.

A most preferred method of producing the compounds of the present invention involves the use of optionally substituted dibenzoxazepine N-carboxylic acid hydrazides as starting materials. The preparation of these compounds is disclosed in U.S. Pat. No. 3,534,019.

Acylation of the aforementioned hydrazides with the appropriate acylating agent in an inert medium affords the desired N,N'-diacyl hydrazines. When a cyclic acid anhydride is employed as the acylating agent, the carboxyalkanoyl or carboxyalkenoyl hydrazines are obtained. The instant sulfonylhydrazides are conveniently prepared by using, as the acylating agent, the appropriate sulfonyl halides. When acylation is accomplished with the use of a halo, phenoxy, or halophenoxy substituted alkanoyl halide, the corresponding substituted hydrazines are respectively produced.

The acid chlorides and acid anhydrides are most preferred acylating agents. Preferred bases are triethylamine, collidine, lutedine, potassium carbonate, sodium bicarbonate and sodium carbonate, and convenient solvents are benzene-methylene chloride, acetonitrile and benzene.

Typical of the reactions providing the carboxyalkanoyl hydrazine derivatives is that of 8-chloro-10,11-dihydrodibenz[b,f][1,4]oxazepine-10-carboxylic acid hydrazide with glutaric anhydride thus affording 1-(4-carboxybutyryl)-2-(8-chloro-10,11-dihydrodibenz[b,f][1,4]-oxazepine-10-carbonyl)hydrazine. In a similar manner, when 8-chloro-10,11-dihydrodibenz[b,f][1,4]oxazepine-10-carboxylic acid hydrazide is reacted with 5-chloropen=tanoyl chloride, phenoxyacetyl chloride, or p-chlorophen=oxyacetyl chloride, 1-(5-chloropentanoyl)-2-(8-chloro-10,11-dihydrodibenz[b,f][1,4]oxazepine-,10-carbonyl)hydrazine, 1-phenoxyacetyl-2-(8-chloro-10,11-dihydrodibenz[b,f][1,4]oxazepine-10-carbonyl)hydrazine, and 1-(p-chlorophenoxyacetyl)-2-(8-chloro-10,11-dihydrodibenz[b,f][1,4]oxazepine-10-carbonyl)hydrazine, respectively, are obtained.

Also, the compounds of the present invention may be prepared by treating the dibenzoxazepine carbonyl chloride in a basic medium with the appropriate acyl hydrazide. This method is particularly convenient when the alkanoyl chlorides are difficult to prepare.

The novel compounds of this invention are valuable pharmacological agents. They are active prostaglandin and 5-hydroxytryptamine antagonists. In addition, they exhibit anti-arrhythmic, anti-inflammatory and anti-diarrheal activity. They possess greater potency than previously disclosed compounds and also exhibit minimal undesirable effects upon the central nervous system.

The prostaglandin and 5-hydroxytryptamine antagonist activity is demonstrated in the following procedure which is substantially the same as that described by J. H. Sanner, Arch. int. Pharmacodyn., 180 (1), 46 (1969):

Female albino guinea pigs weighing 200–500 g. are sacrificed by cervical dislocation and the ileum is quickly removed and placed in modified Tyrode solution containing ½ the usual amount of magnesium ions. Segments of ileum, about 2 centimeters long are cut and mounted in a 2 or 4 ml. tissue bath containing the modified Tyrode solution. The solution is maintained at 37° and bubbled with a gaseous mixture of 95% oxygen and 5% carbon dioxide. Contractions are detected isotonically. Approximately equal submaximal contractions are obtained in preliminary trials by adjusting the doses of prostaglandin $E_2$ ($PGE_2$) and 5-hdroxytryptamine added to the bath. Two central contractions are obtained at 3.5 minute intervals. A solution or suspension of the test compound in the bathing solution is then substituted for the original modified Tyrode solution. The test suspension is kept in constant contact with the tissue for the remainder of the experiment except for brief periods to drain the bath in preparation for rinsing with fresh test suspension. Three more contractions are elicited to each agonist in the presence of the test compound without interrupting the time sequence. The last two sets of treated responses are compared with the two sets of control responses. The first set of treated responses is not used for comparisons, being used only to maintain the timed sequence of injections during the period allowed for the tissue to become equilibrated with the antagonist. A compound is rated active if the mean of contractions produced by any agonist is reduced 75% or more by the test compound.

The anti-inflammatory properties of the instant compounds is demonstrated by their activity in an assay adapted from that described by Tonelli et al., Endocrinology, 77, 625 (1965) and detailed as follows:

0.1 Cubic centimeter of a phlogistic vehicle consisting of 4 parts of pyridine, 1 part of distilled water, 5 parts of diethyl ether and 10 parts of 2% Croton oil in ether (v/v) is applied topically to the right ear of each of a group of 8–10 rats, while the contralateral left ear remains untreated and serves as the control. For the determination of activity of the test compound a similar group of animals is treated with the same volume of the phlogistic vehicle containing 400 meg. of the compound. In addition, a third group of animals is treated in the same manner with the same volume of the phlogistic vehicle containing 80 meg. of a standard topical anti-inflammatory agent (hydrocortisone).

Six hours after treatment the animals are lightly etherized and both ears are removed by means of a scissors, using anatomical structures of the ears as the line of demarcation. The ears are weighed individually and the present increase in weight of inflamed ear as compared to the untreated contralateral ear is determined. The percent increase in ear weight of the compound treated group is then compared statistically by Wilcoxon Rank Sum Analysis with the percent increase in ear weight of the control group which received the phlogistic vehicle alone.

The anti-diarrheal properties of the compounds of this invention are apparent from their activity in the following assay procedure.

To groups of 10 Charles River male mice weighing 30–40 g. of administered intraperitoneally a selected dose of the test compound suspended in an aqueous medium containing 0.1% of polysorbate 80 (polyoxyethylene sorbitan mono-oleate). A constant volume of 0.1 ml./10 g. body weight of the suspension is used for each animal.

Fifteen minutes after administration of the test compound, the mice are injected intrapertioneally with 50 μg./kg. body weight of prostaglandin $E_2$, the dose previously demonstrated to produce diarrhea in more than 95% of control animals. Thereafter, each mouse is placed on a disc of filter paper in an individual glass cylinder and observed for a period of 15 minutes for the presence or absence of diarrhea. The compound is tested at a variety of dosage levels until at least one dose results in protection of more than 50% of the mice and one dose in less than 50% of the mice. The protective dose - 50 ($pD_{50}$) is calculated by the method of D. J. Finney, "Statistical Method in Biological Assay", Chapter 17, Hafner Publishing Co., New York, 1964, using the proportion of mice protected by each dose of compound.

The following examples will further illustrate the present invention. They should not be construed as limiting the invention either in spirit or in scope as modifications both in materials and methods will be apparent to those skilled in the art. In these examples temperatures are indicated in degrees Centigrade (°C.) and quantities of materials in parts by weight unless parts by volume is specifically expressed.

EXAMPLE 1

To 1 part of 8-chloro-10,11-dihydrodibenz[b,f][1,-4]oxazepine-10-carboxylic acid hydrazine dissolved in 50 parts by volume of 1:1 benzene-methylene chloride solution, is added in one portion 0.344 part of maleic anhydride. The reaction mixture is stirred at room temperature for 24 hours, and the solvent is evaporated to yield an oil which is crystallized from benzene-ethyl acetate solution. Recrystallization from ethyl acetate-cyclohexane-ethanol solution yields 1-(3-carboxypropenoyl)-2-(8-chloro-10,11-dihydrodibenz[b,f]-[1,4]oxazepine-10-carbonyl)hydrazine, melting at about 171°–172°. This compound can be represented by the following structural formula

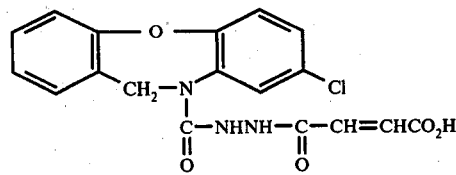

EXAMPLE 2

When an equivalent quantity of glutaric anhydride is substituted in the procedure of Example 1, there is obtained 1-(4-carboxybutyryl)-2-(8-chloro-10,11-dihydrodibenz[b,f][1,4]oxazepine-10-carbonyl)hydrazine, melting at about 173°–176° with decomposition. This compound is structurally represented by the following formula

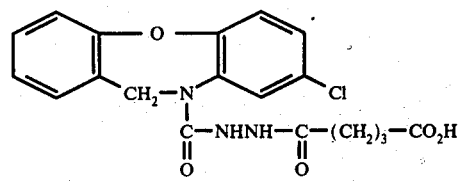

EXAMPLE 3

By substituting an equivalent quantity of succinic anhydride in the procedure of Example 1, there is produced 1-(3-carboxypropionyl)-2-(8-chloro-10,11-dihydrodibenz[b,f][1,4]oxazepine-10-carbonyl)hydrazine, melting at about 177°–179° with decomposition. This compound is represented by the following structural formula

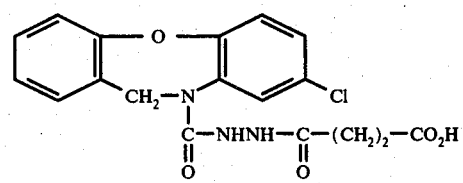

EXAMPLE 4

To a solution of 0.5 part of 8-chloro-10,11-dihydrodibenz[b,f][1,4]oxazepine-10-carboxylic acid hydrazide and 19.6 parts of acetonitrile is added 0.298 part of sodium bicarbonate followed by 0.6 part of phenoxyacetyl chloride. The solution is stirred for 48 hours at room temperature, after which time the solvent is removed under reduced pressure and the resulting residue is purified by recrystallization from ethyl acetate-cyclohexane is afford 1-phenoxyacetyl-2-(8-chloro-10,11-dihydrodibenz[b,f][1,4]oxazepine-10-carbonyl)hydrazine, melting at about 157°–158° with decomposition. This compound is represented by the following structural formula

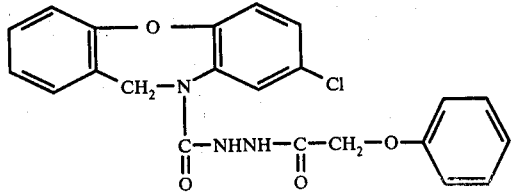

EXAMPLE 5

Upon substituting equivalent quantities of triethylamine and p-chlorophenoxyacetyl chloride and otherwise following the procedure of Example 4, one obtains 1-(p-chlorophenoxyacetyl)-2-(8-chloro-10,11-dihydrodibenz[b,f][1,4]oxazepine-10-carbonyl)hydrazine, when melts at about 138°–139° with decomposition and is represented by the following structural formula

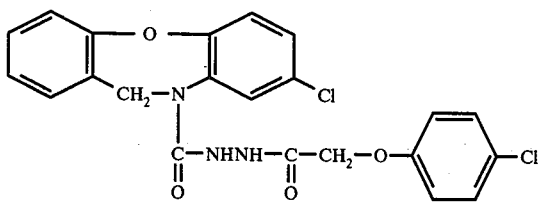

EXAMPLE 6

By substituting equivalent quantities of sodium carbonate and 5-chloropentanoyl chloride in the procedure of Example 4, there is produced 1-(5-chloropentanoyl)-2-(8-chloro-10,11-dihydrodibenz[b,f][1,4]oxazepine-10-carbonyl)hydrazine, which has a melting point at about 148°–149° and is structurally represented by the following formula

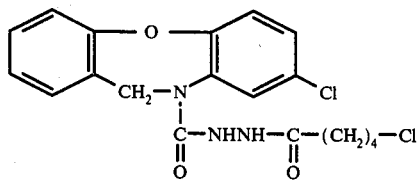

EXAMPLE 7

When one substitutes 8-trifluoromethyl-10,11-dihydrodibenz[b,f][1,4]oxazepine-10-carboxylic acid hydrazide, sodium carbonate and 5-chloropentanoyl chloride in the procedure of Example 4, there is produced 1-(5-chloropentanoyl)-2-(8-trifluoromethyl-10,11-dihydrodibenz[b,f][1,4]oxazepine-10-carbonyl)hydrazine. This compound melts at about 121.5°–123.5° and is represented by the following structural formula

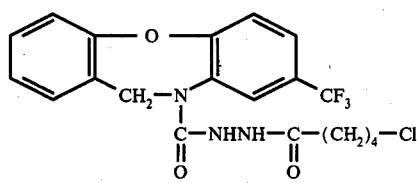

EXAMPLE 8

When equivalent quantities of 3-phenoxypropionyl chloride and sodium carbonate are substituted in the procedure of Example 4, 1-(3-phenoxypropionyl)-2-(8-chloro-10,11-dihydrodibenz[b,f][1,4]oxazepine-10-carbonyl)hydrazine is afforded.

EXAMPLE 9

By substituting equivalent quantities of 3-(p-chlorophenoxy)propionyl chloride and sodium carbonate and otherwise following the procedure of Example 4, there is obtained 1-(3-[p-chlorophenoxy]-propionyl)-2-(8-chloro-10,11-dihydrodibenz[b,f][1,4]-oxazepine-10-carbonyl)hydrazine.

EXAMPLE 10

Substitution of equivalent quantities of 6-chlorohexanoyl chloride and sodium carbonate in the procedure of Example 4 produces 1-(6-chlorohexanoyl)-2-(8-chloro-10,11-dihydrodibenz[b,f][1,4]oxazepine-10-carbonyl)hydrazine.

EXAMPLE 11

When equivalent quantities of n-butylsulfonyl chloride and sodium carbonate are substituted in the procedure of Example 4, there is produced 1-(n-butylsulfonyl)-2-(8chloro-10,11-dihydrodibenz[b,f][1,4]oxazepine-10-carbonyl)hydrazine melting at about 148°–150°.

EXAMPLE 12

To a solution containing 1.45 parts of 8-chloro-10,11-dihydrodibenz[b,f][1,4]oxazepine-10-carboxylic acid hydrazide dissolved in 50 parts by volume of benzene is added successively 0.7 part by volume of triethylamine and 0.81 part of cinnamoyl chloride. The resulting reaction mixture is stirred at room temperature for about 48 hours, then is washed successively with dilute hydrochloric acid, dilute aqueous sodium hydroxide, water and saturated aqueous sodium chloride. Drying over anhydrous sodium sulfate followed by removal of the solvent by distillation under reduced pressure affords a residue, which is purified by adsorption on a silicic acid chromatographic column and elution with ethyl acetate-benzene mixtures. The 10% acetate in benzene eluate, upon removal of the solvents, affords 1-cinnamoyl-2-(8-chloro-10,11-dihydrodibenz[b,f][1,4]oxazepine-10-carbonyl)hydrazine.

EXAMPLE 13

The substitution of an equivalent quantity of crotonyl chloride in the procedure of Example 12 affords, after chromatography on a silicic acid column as described in that Example, 1-crotonyl-2-(8-chloro-10,11-dihydrodibenz[b,f][1,4]oxazepine-10-carbonyl)hydrazine, melting at about 105°–110°. When that material is dried under vacuum at approximately 100°–105°, the pure product, melting at about 178°–182°, is obtained.

EXAMPLE 14

To a solution containing 5 parts of 8-chloro-10,11-dihydrodibenz[b,f][1,4]oxazepine-10-carbonyl chloride in 60 parts by volume of acetonitrile is added successively 1.68 parts of cyanoacetohydrazide and excess sodium bicarbonate. The resulting reaction mixture is stirred at room temperature for about 24 hours, then is diluted with benzene and stirred for approximately 30 minutes longer. The resulting mixture is filtered and the filtrate is concentrated to dryness under reduced pressure to afford the crystalline product. Purification by recrystallization from ethanol using declorizing carbon, affords pure 1-cyanoacetyl-2-(8-chloro-10,11-dihydrodibenz[b,f][1,4]-oxazepine-10-carbonyl)hydrazine, melting at about 208°–210°.

EXAMPLE 15

To a solution containing 2.9 parts of 8-chloro-10,11-dihydrodibenz[b,f][1,4]oxazepine-10-carboxylic acid hydrazide dissolved in 50 parts by volume of acetonitrile containing excess aqueous potassium carbonate is added 0.95 parts of 1-methyl-1-phenoxyacetyl chloride and the resulting reaction mixture is stirred at room temperature for about 48 hours. The solvent is removed under reduced pressure and the resulting residue is purified by chromatography on a silica gel column followed by elution with hexane-benzene solution. The 10% hexane in benzene eluate affords 1-(1-methyl-1-phenoxyacetyl)-2-(8-chloro-10,11-dihydrodibenz[b,f][1,4]oxazepine-10-carbonyl)hydrazine, melting at 150°–153°.

EXAMPLE 16

When an equivalent quantity of p-toluenesulfonyl chloride is substituted in the procedure of Example 15, there is produced 1-p-toluenesulfonyl-2-(8-chloro-10,11-dihydrodibenz[b,f][1,4]oxazepine-10-carbonyl)hydrazine, which, after recrystallization from benzene-cyclohexane, affords the pure product, melting with decomposition at about 206°–209°.

EXAMPLE 17

When an equivalent quantity of benzylsulfonyl chloride is substituted in the procedure of Example 16 and the reaction is continued for approximately 48 hours at room temperature, there is produced, after recrystallization from benzene, pure 1-benzylsulfonyl-2-(8-chloro-10,11-dihydrodibenz[b,f][1,4]oxazepine-10-carbonyl)hydrazine, melting with decomposition at about 118°–120°.

EXAMPLE 18

When equivalent quantities of methanesulfonyl chloride and sodium carbonate, as the acid acceptor are substituted in the procedure of Example 12, there is produced, after recrystallization from benzene, 1-methanesulfonyl-2-(8-chloro-10,11-dihydrodibenz[b,f][1,4]-oxazepine-10-carbonyl)hydrazine, melting with decomposition at about 108°–110°.

EXAMPLE 19

The substitution of an equivalent quantity of 3-chloropropylsulfonyl chloride in the procedure of Example 12 affords, after recrystallization from benzene-cyclohexane, 1-(3-chloropropylsulfonyl)-2-(8-chloro-10,11-dihydrodibenz[b,f][1,4]oxazepine-10-carbonyl)hydrazine, melting with decomposition at about 167°–170°.

EXAMPLE 20

When an equivalent quantity of 4-chlorobutyryl chloride and also an equivalent quantity of sodium carbonate, as the acid acceptor, are substituted in the procedure of Example 4, there is produced 1-(4-chlorobutyryl)-2-(8-chloro-10,11-dihydrodibenz[b,f][1,4]oxazepine-10-carbonyl)hydrazine, melting, after recrystallization from either benzene-cyclohexane or benzene-hexane, at about 154°–156°.

EXAMPLE 21

By substituting an equivalent quantity of 5-bromopentanoyl chloride in the procedure of Example 20, there is produced 1-(5-bromopentanoyl)-2-(8chloro-10,11-dihydrodibenz[b,f][1,4]oxazepine-10-carbonyl)hydrazine, melting at about 147°–149°.

EXAMPLE 22

When an equivalent quantity of 5-chloro-3-methylpentanoyl chloride and an equivalent quantity of potassium carbonate, as the acid acceptor, are substituted in the procedure of Example 18, there is obtained, after recrystallization from cyclohexane, 1-(5-chloro-3-methylpentanoyl)-2-(8-chloro-10,11-dihydrodibenz[b,f][1,4]-oxazepine-10-carbonyl)hydrazine, melting at about 125°–128°.

EXAMPLE 23

When the procedure of Example 12 is carried out, substituting equivalent quantities of chloroacetic anhydride as the acylating agent and sodium bicarbonate as the acid acceptor, there is produced 1-chloroacetyl-2-(8-chlor-10,11-dihydrodibenz[b,f][1,4]oxazeine-10-carbonyl)hydrazine, melting at about 174°–176°.

EXAMPLE 24

To a suspension of 8.16 parts of 8-chloro-10,11-dihydrodibenz-[b,f][1,4]oxazepine-10-carboxylic acid hydrazide in 200 parts of dry benzene is added successively 2.79 parts by volume of triethylamine and 2.82 parts by volume of trifluoroacetic anhydride. The reaction mixture is then stirred at room temperature for about 24 hours, at the end of which time approximately 40 parts of water followed by 20 parts by volume of 10% aqueous hydrochloric acid are added. The solution is then filtered and the resultant layers separated. The benzene layer is dried over anhydrous sodium sulfate and the solvent removed by distillation under reduced pressure. The resulting residual oil is purified by trituration with hexane, followed by recrystallization from benzene, thus affording 1-trifluoroacetyl-2-(8-chloro-10,11-dihydrodibenz[b,f]1,4]oxazepine-10-carbonyl)hydrazine, melting at about 158°–160°.

EXAMPLE 25

To a suspension of 2.88 parts of 8-chloro-10,11-dihydrodibenz[b,f][1,4]oxazepine-10-carboxylic acid hydrazide with 100 parts by volume of dry benzene is added about 1 part of formic acetic anhydride, prepared from 10.2 parts of acetic anhydride and 4.6 parts of formic acid. The reaction mixture is stirred until no evidence of starting material is detected, at which time 100 parts of water is added with vigorous stirring. Stirring is continued for about 1 hour, at the end of which time the mixture is filtered and the resulting product is dried to afford 1-formyl-2-(8-chloro-10,11-dihydrodibenz[b,f][1,4]oxazepine-10-carbonyl)hydrazine, melting at about 177°–181°.

EXAMPLE 26

To a suspension of 2.88 parts of 8-chloro-10,11-dihydrodibenz[b,f][1,4]oxazepine-10-carboxylic acid hydrazide in 100 parts by volume of benzene is added 2.33 parts of perfluorobutyryl chloride, followed by about 1.5 parts of triethylamine. The reaction mixture is stirred at room temperature for about 48 hours and 100 parts of water is then added with vigorous stirring. The benzene layer is separated, dried over anhydrous sodium sulfate and distilled to dryness under reduced pressure, thus affording 1-perfluorobutyryl-2-(8-chloro-10,11-dihydrodibenz[b,f]1,4]oxazepine-10- carbonyl)hydrazine, which compound is exemplified by the following structural formula

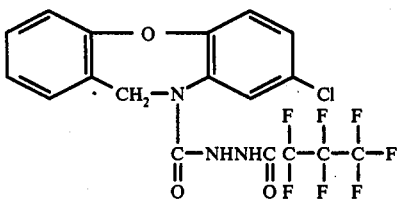

EXAMPLE 27

To a solution of 2.88 parts of 8-chloro-10,11-dihydrodibenz[b,f][1,4]oxazepine-10-carboxylic acid hydrazide in 88 parts of benzene is added 4.32 parts by volume of perfluorooctanoyl chloride and excess solid sodium carbonate. The mixture is stirred at room temperature for about 72 hours, the diluted with water and the organic layer is separated and dried over anhydrous sodium sulfate. Distillation of the solvent under reduced pressure affords the desired 1-perfluorooctanoyl-2-(8-chloro-10,11-dihydrodibenz[b,f][1,4]oxazepine-10-carbonyl)hydrazine, characterized by the following formula.

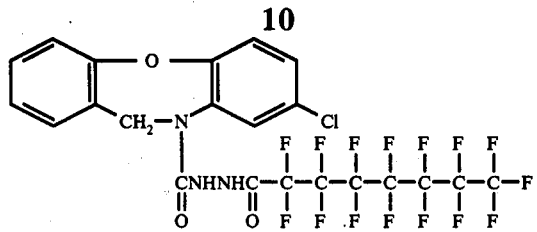

What is claimed is:
1. A compound of the formula

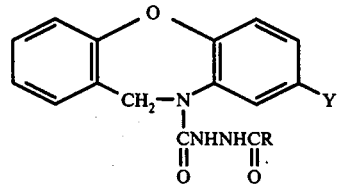

wherein Y is selected from the group consisting of halogen and trifluoromethyl radicals, R is phenalkenyl having from 2–12 carbon atoms in the alkenyl portion.

2. As in claim 1, the compound which is 1-cinnamoyl-2-(8-chloro-10,11-dihydrodibenz[b,f][1,4-oxazepine-10-carbonyl)hydrazine.

* * * * *